United States Patent
Theeuwes

[11] 4,309,996
[45] Jan. 12, 1982

[54] SYSTEM WITH MICROPOROUS RELEASING DIFFUSOR

[75] Inventor: Felix Theeuwes, Los Altos, Calif.

[73] Assignee: Alza Corporation, Palo Alto, Calif.

[21] Appl. No.: 144,210

[22] Filed: Apr. 28, 1980

[51] Int. Cl.³ ............................................. A61M 7/00
[52] U.S. Cl. .................................................. 128/260
[58] Field of Search ...................... 128/127, 130, 260; 424/19, 22

[56] References Cited

U.S. PATENT DOCUMENTS

| | | | |
|---|---|---|---|
| 3,760,805 | 9/1973 | Higuchi | 128/260 |
| 3,929,132 | 12/1975 | Higuchi | 128/260 |
| 4,111,201 | 9/1978 | Theeuwes | 128/260 |
| 4,111,202 | 9/1978 | Theeuwes | 128/260 |
| 4,180,073 | 12/1979 | Michaels | 128/260 |
| 4,203,439 | 5/1980 | Theeuwes | 128/260 |
| 4,210,139 | 7/1980 | Higuchi | 128/260 |
| 4,217,898 | 8/1980 | Theeuwes | 128/260 |

Primary Examiner—C. Fred Rosenbaum
Attorney, Agent, or Firm—Paul L. Sabatine; Edward L. Mandell

[57] ABSTRACT

A system is disclosed for delivering a beneficial agent at a substantially constant rate over time. The system comprises (1) a wall formed of a microporous polymer, or (2) a wall formed in part of a microporous polymer with the remaining part of the wall formed of a semipermeable polymer. The wall in (1) surrounds a compartment comprising a flexible partition that separates the compartment into a first space containing the beneficial agent and a second space containing a swellable polymer. The wall in (2) surrounds a compartment comprising a flexible partition that separates the compartment into a first space in contact with the microporous wall and containing the beneficial agent, and a second space in contact with the semipermeable polymer containing an osmotically effective solute, or a swellable polymer. In operation, agent is delivered from the system by (a) fluid diffusing through the microporous wall into the second space causing the polymer to swell, or by (b) fluid being imbibed through the semipermeable wall into the second space causing the solute to dissolve and form a solution, or causing the polymer to swell, wherein in (a) or (b), the second space expands against the partition urging it to move into the first space and maintain the agent in a saturated state at the microporous wall, with the agent diffusing from the first space through fluid filled micropaths in the wall from the system at a substantially zero order rate over a prolonged period of time.

19 Claims, 6 Drawing Figures

SYSTEM WITH MICROPOROUS RELEASING DIFFUSOR

FIELD OF THE INVENTION

The invention pertains to a system comprising a microporous diffusor for delivering a beneficial agent to a fluid environment of use at a zero order rate for an increased length of time at that rate.

BACKGROUND OF THE INVENTION

Today, more research than ever before is devoted for providing systems that can deliver a beneficial agent at a controlled rate of release to an environment of use over a specified period of time. For example, in U.S. Pat. Nos. 3,845,770 and 3,916,899 issued to inventors Felix Theeuwes and Takeru Higuchi, osmotic systems manufactured in the form of osmotic systems are disclosed for delivering a beneficial agent at a controlled rate to an environment of use. The systems disclosed in these patents comprise a semipermeable wall that surround a compartment containing the agent. The wall is permeable to an external fluid, substantially impermeable to agent, and there is a passageway through the wall for delivering the agent from the system. These systems release the agent by fluid being imbibed through the wall into the compartment, at a rate determined by the permeability of the wall and the osmotic pressure gradient across the wall, to produce a solution of the agent, that is dispensed through a passageway from the system. In U.S. Pat. No. 4,111,202, issued to Patentee Felix Theeuwes, an osmotic system is disclosed comprising a semipermeable wall that surrounds a first and second compartment. The first compartment contains a drug and the second compartment contains an osmotically effective solute. A passageway through the semipermeable wall connects the exterior of the system with the first compartment. The system releases agent by fluid being imbibed into the first compartment to prepare drug formulation and by fluid being imbibed into the second compartment causing it to increase in volume, expand into and decrease the volume of the first compartment, whereby the agent is delivered through the passageway from the system.

While the above systems are outstanding and represent a pioneer advancement in the delivery art, and while they are endowed with ideal delivery kinetics useful for delivering numerous and diverse beneficial agents at a controlled and continuous rate to many environments of use, there is an occasional instance where the delivery kinetics of the systems can be unexpectedly modified to lead to more desirable results. For example, one of the important factors that should be considered in designing a controlled release system is to maintain a constant thermodynamic activity of beneficial agent within the system. The pressure of this constant activity source establishes a steady state, so that agent is released from the system at a constant rate over time. This phenomenon is commonly referred to as zero order release.

If, however, a constant thermodynamic activity of agent is not maintained within the system and the released agent is not replenished, because the system lacks excess agent or a means for keeping the agent in a saturated state, the release rate falls exponentially and the amount of agent released can also become unpredictable over time. These latter conditions occur because less and less agent is available at the releasing diffusion boundary layer of the system and the quantity available for diffusion can be dependent on the degree of agitation. This release pattern is called first order release.

It wil be appreciated by those versed in the delivery art that in many applications, for example in the pharmaceutical, veterinary and agriculture industries, the zero order release is the most preferred release. This is so because precise delivery of an agent in known and constant amounts per unit time can lead to improve usage, and also in many instances minimize deleterious effects to the environment, organisms and plants. Also, through controlled release, the efficacy of agents may be enhanced, and the use of agents exhibiting high potencies or low stabilities may prove more managable and economical over time. It will be further appreciated in view of this presentation, that if a system is provided that can exhibit a substantially zero order release over time, the system would have a positive commercial use and also represent a major contribution to the delivery art.

OBJECT OF THE INVENTION

Accordingly, it is an immediate object of this invention to provide a system that has useful thermodynamic physicochemical properties for delivering a beneficial agent over time.

Another object of the invention is to provide a system that has a delayed, diminishing boundary layer for increasing the amount of agent delivered at a zero order release rate over time.

Yet another object of this invention is to provide a system having a constant activity source by providing a system comprising a wall and an internal expandable force that operates to maintain agent within the system in a saturated state at the releasing agent wall interace in the system.

Still another object of the invention is to make available a system for delivering an agent, whose release is controlled by Fickian diffusion through fluid-filled paths in a microporous wall, with the agent activity at the internal boundary layer kept at substantially saturated level for an increased agent release period.

Yet still another object of the invention is to make available a system that delivers a beneficial agent at a prolonged substantially constant rate by delaying the appearance of a diminishing agent boundary interface and its accompanying drop in the delivery rate by providing a system that substantially maintains the agent at a saturated level at the boundary interface for an increased length of time.

Still yet another object of this invention is to make available a delivery system that exhibits a more constant, predictable release rate profile of useful agent.

Still another object of the invention is to provide a novel and useful delivery system manufactured in the form of a delivery device with a diffusor for delivering agent from the system over time.

Other objects, features, aspects and advantages of the invention will be more apparent to those versed in the art from the following detailed specification, taken in conjunction with the figures and the accompanying claims.

SUMMARY OF THE INVENTION

This invention concerns a system for delivering a beneficial agent to an environment of use. The system consists essentially of a microporous wall, or a part microporous part semipermeable wall surrounding a compartment having a space containing the agent separated by a partition from a space containing an expandable entity. The entity consists of an osmotically effective solute, or a swellable polymer. In operation, agent is released from the system by the combined integrated physical-chemical actions of the system, the agent and the entity. The actions embrace agent diffusing through paths in the microporous wall, the entity expanding or continuously filling its space, and expanding into the agent space, thereby delaying the appearance of a diminishing, diffusional boundary layer. The combined actions cause the agent to be delivered from the system at a controlled and substantially zero-order rate of release over an increased, prolonged period of time.

BRIEF DESCRIPTION OF THE DRAWINGS

In the drawings, which are not drawn to scale, but are set forth to illustrate various embodiments of the invention, the figures are as follows:

FIG. 2a is an opened view of the system of FIG. 1, which FIG. 2a illustrates the internal structure of the system consisting essentially of two spaces separated by a partition, with one space containing a means for increasing the fraction of agent delivered at zero order over time by maintaining the saturated state of agent in the integral unit manufactured as a device;

In the drawings and specification, like parts in related figures are identified by like numbers. The terms appearing earlier in the specification and in the description of the drawings, as well as embodiments thereof, are further discussed elsewhere in the disclosure.

DETAILED DESCRIPTION OF THE DRAWINGS

Figure 1:
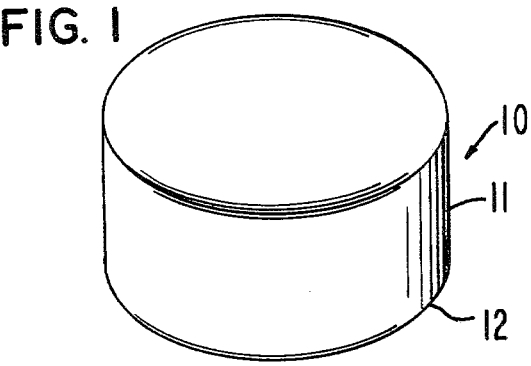
FIG. 1 is a view of a delivery system designed and shaped for administering orally a beneficial drug to a warm-blooded animal.

Turning now to the drawings in detail, which drawings are examples of various delivery systems of the invention, and which examples are not to be considered limiting, one example of a system is indicated in FIG. 1 by the numeral 10. In FIG. 1, system 10 comprises a body 11, that is shaped, sized, structured and adapted for easy placement and prolonged retention in an environment of use for the controlled, continuous delivery of a beneficial agent thereto.

Figure 2A:
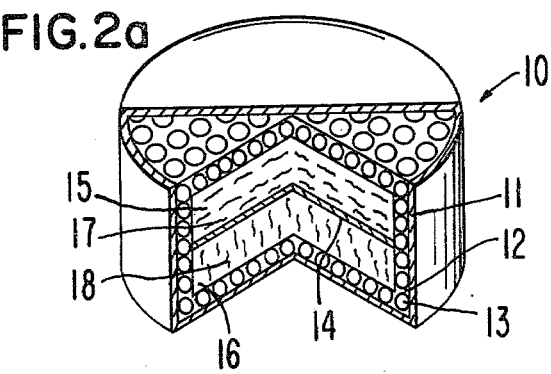

In FIG. 2a system 10 of FIG. 1 is seen in opened-section with a part of its outer layer removed for elucidating the total structure of system 10. In FIG. 2a, system 10 comprises a body 11 having an exterior wall 12 that surrounds an internal space having a partition 14 that separates the space into a first space 15 and a second space 16. Space 16 contains a swellable polymer 18, that on swelling in the presence of water exerts pressure on partition 14 causing it to move and occupy volume in space 15. The actions of partition 14 and polymer 18 combine to decrease the volume of space 15, thereby functioning to maintain beneficial agent 17 in a saturated state in space 15, especially during the time system 10 is in operation in a prechosen environment of use.

In FIG. 2a, wall 12 of device 10 is formed of a microporous polymeric material containing a plurality of microscopic-sized interconnected pores or voids. The pores, illustrated as circles 13 for discussion herein, can be continuous with openings on both sides of wall 12, the pores can be interconnected through tortuous paths of regular and irregular shapes, including curved, curved-linear, randomly oriented continuous paths, hindered connected paths and pores, and other paths and pores discernible by microscopic examination. Generally, materials possessing from 5 to 95% pores, more preferably a void space of 30% to 90%, and having a pore size of 100 angstroms to 200 microns can be used for making wall 12. The pores and connecting intrawall paths can be preformed in the polymer, which microporous polymer is then manufactured as wall 12 of system 10. In another, and presently preferred embodiment, wall 12 contains a multiplicity of pore-formers, not shown, that are dissolved or leached from wall 12, which is integrally manufactured as system 10. In this embodiment, the pore-formers are removed when system 10 is in the environment of use, thereby forming microporous wall 12 in the environment.

The microporous paths of wall 12 are prefilled or filled in the environment of use with a diffusive medium permeable to the passage of agent 17. The medium is generally non-toxic and it does not adversely effect the system, the wall, the agent and the environment. In one embodiment, the medium is a liquid phase comprised of a solution, a colloidal medium, or a sol, the medium can be polar, semi-polar or non-polar, or it can be a liquid present in the environment of use, including water, biological fluids, saline, and buffers.

Partition 14 of system 10 consists, in one embodiment, of a film made of a semipermeable polymer that is essentially impermeable to the passage of agent, osmotic solute and polymer and is permeable to the passage of fluid that enters system 10; and, in another embodiment partition 14 is made of a film impermeable to agent, solutes, polymers and fluid. Partition 14 is suitably joined to wall 12 during manufacture of system 10, and in a presently preferred embodiment it can contain a plasticizer that imparts flexibility and expandability to partition 14. In operation, when compartment 16 contains polymer 18, the polymer 18 absorbs fluid that enters compartment 16 causing 18 to swell, expand and fill compartment 16, and also, swell and expand against partition 14, causing it to move and occupy the space of compartment 15. This action correspondingly reduces the amount of space available for agent 17, and this continual decrease in space substantially keeps agent 17 in a substantially saturated phase.

Figure 2B:
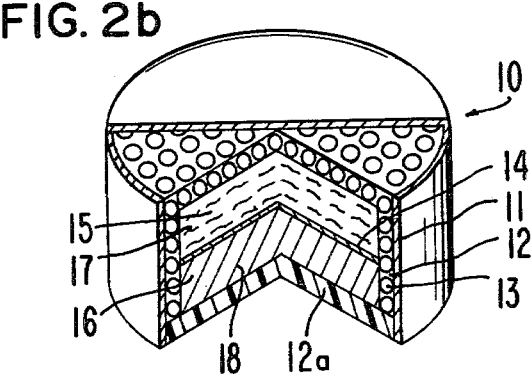
FIG. 2b is the system of FIG. 1 with a section removed for depicting the internal structure of the system manufactured with a partition, a different external wall structure, an agent housing space and a contacting expanding means for increasing the fraction of agent present in a saturated state in the system.

In FIG. 2b, another system 10 is provided according to the mode and the manner of invention. System 10 of FIG. 2b is similar to system 10 of FIG. 2a, with system 10 of FIG. 2b embracing other structural embodiments. The embodiments of FIG. 2b include wall 12 having at least one surface 12a formed of a semipermeable polymer. When wall 12a is formed of a semipermeable polymer, space 16 contains a member selected from the group consisting essentially of an osmotically effective solute and a swellable polymer 18. When space 16 houses the solute or the swellable polymer, partition 14 is formed of a member selected from the group consisting of a semipermeable polymer, and an impermeable polymer. When space 16 contains an osmotic solute, in operation it imbibes fluid through semipermeable wall 12a in a tendency towards osmotic equilibrium to dissolve the solute and form a solution that fills space 16, apply pressure against partition 14, urging it to move into space 15 and decrease its volume, thereby keeping the beneficial agent present at the microporous wall 12. When space 16 contains a swellable polymer, it absorbs fluid, expands, but does not dissolve in fluid that enters space 16. The expanding polymer pushes against partition 14 causing it to move into space 15, thereby keeping agent 17 in a saturated state at the release rate wall.

Figure 3:
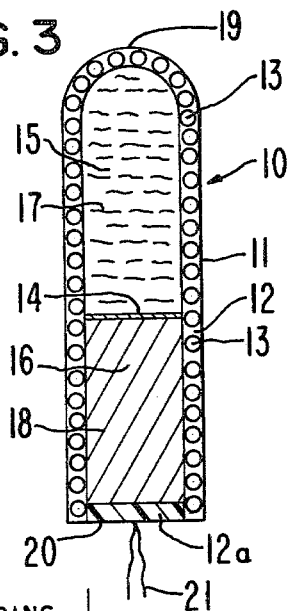
FIG. 3 illustrates, in opened section, a system provided by the invention, said system shaped and dimensioned for dispensing a drug in a body passageway such as the vagina, or the ano-rectal passageway.

FIG. 3 shows a system 10 designed, shaped, sized and styled for easy placement and comfortable retention in a body passageway, such as the vagina, or the ano-rectal passageways. System 10 has a elongated, cylindrical, self-sustaining shape with a pointed lead end 19, a trailing end 20, and it is equipped with manually controlled cords 21 for easily removing device 10 from a body passageway. Device 10 of FIG. 3 is structurally identical with device 10 of FIG. 1, 2a and 2b, and it operates in a like manner, with element 16 expanding for continually occupying area and void space in element 15 created by agent 17 diffusing through micropores 13. Device 10 of FIG. 3 contains a drug designed for release and absorption by the vaginal or the rectal mucosa.

Figure 4:
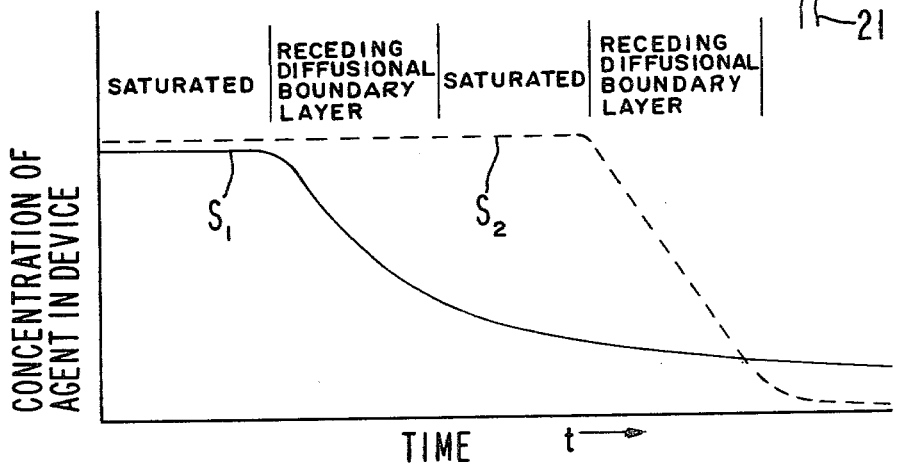
FIG. 4 is a graph that illustrates the increase in time that can be achieved from $S_1$ to $S_2$ if an agent is maintained in a saturated state, thereby concomitantly delaying a premature appearance of the receding diffusional boundary layer; and, FIG. 5 is an opened view showing a longitudinal section of a screw extruder used for blending agent formulations housed in the systems of the invention.

FIG. 4 compares the results obtainable with a system made without the space consuming, saturation maintaining internal structure provided by this invention, with the results obtainable with a system made with the space consuming saturation maintaining internal structure provided by this invention. The figure depicts for the former system a saturation state $S_1$ having an early receding diffusional boundary layer, and for the latter system saturated state $S_2$, which for this system represents an increased length of time the saturation state is present from $S_1$ to $S_2$. This increase in time t, is accompanied by a delay in the appearance of the receding diffusional boundary layer, and a prolonged length of time the agent is delivered at a zero order rate of release.

Figure 5:
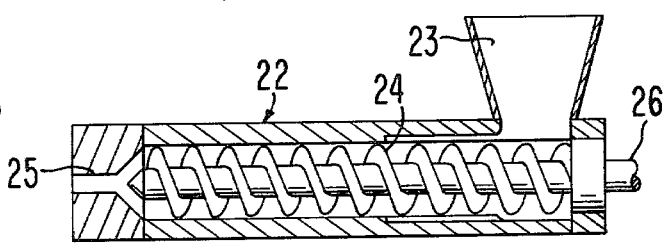

FIG. 5 illustrates an extruder that can be used for blending agent formulations housed in delivery system 10. In FIG. 5, extruder 22 consists of a filling hopper 23, a screw 24 longitudinally extended in extruder 22, a drive journal 26 for turning screw 24 and an extruder die 25 at the terminus of screw 24 for extruding blended formulations. In use, agent and blended ingredients, in powder or granule form, are fed into hopper 23 for continuous feeding to screw 24, where they roll around while the screw is turning, thereby homogenizing and blending the ingredients. The ingredients are finally extruded through die 25 as system intermediates that are eventually manufactured into system 10.

While FIGS. 1 through 3 are illustrative of various systems that can be made according to this invention, it is to be understood those systems are not to be construed as limiting the invention, as the systems can take a wide variety of shapes, sizes and forms for delivering an agent, including drugs, to different environments of use. For example, the systems include buccal, implant, eye, artificial gland, cervical, intrauterine, ear, nose, dermal, subcutaneous, and blood delivery systems. The systems can be used in hospitals, veterinary clinics, nursing homes, sickrooms, and the like.

DETAILED DESCRIPTION OF THE INVENTION

In accordance with the practice of the invention, it has now been found that diffusion delivery system 10 can be manufactured with microporous wall 12, formed from microporous polymers that are commercially available, or they can be made by art known methods. The microporous materials can be made, and then manufactured into a system, by etched nuclear tracking, by cooling a solution of a flowable polymer below its freezing point whereby solvent evaporates from the solution in the form of crystals dispersed in the polymer, and then curing the polymer followed by removing the solvent crystals, by cold or hot stretching of a polymer at low or high temperatures until pores are formed, by leaching from a polymer a soluble pore forming component by use of an appropriate solvent, by ion exchange reactions consisting of exchanging a large space occupying ion with a smaller ion, by polyelectrolytic processes, and by dissolving or leaching a pore former from the wall of a system in operation in the environment of use. Processes for preparing microporous materials are described in *Synthetic Polymer Membranes*, by R. E. Kesting, Chapters 4 and 5, 1971 published by McGraw Hill, Inc; *Chemical Reviews, Ultrafiltration*, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,224; and 3,849,528.

Materials useful for making the microporous wall 12 include polycarbonates comprised of linear polyesters of carbonic acid in which carbonate groups recur in the polymer chain, microporous materials prepared by the phosgenation of a dihydroxyl aromatic such as a bisphenol A, microporous poly (vinylchloride), microporous polyamides such as polyhexamethylene adipamide, microporous modacrylic copolymers including those formed from poly(vinylchloride) 60% and acrylonitrite, microporous styrene-acrylic copolymers, porous polysulfones characterized by diphenylene sulfone groups in a linear chain thereof, halogenated poly(vinylidene), polychloroethers, acetal polymers, polyesters prepared by esterification of a dicarboxylic acid or anhydride with an alkylene polyol, poly(alkylenesulfides), phenolic polyesters, microporous poly(saccharides), microporous poly(saccharides) having substituted anhydroglucose units exhibiting a decrease permeability to the passage of water and biological fluids, asymmetric porous polymers, cross-linked microporous olefin polymers, hydrophobic or hydrophilic microporous homopolymers, copolymers having a reduced bulk density, and materials described in U.S. Pat. Nos. 3,595,752; 3,643,178; 3,654,066; 3,709,774; 3,718,532; 3,803,061; 3,852,224; 3,852,388; and 3,852,601, in British Pat. No. 1,126,849, and in *Chem. Abst.*, Vol. 71 427F, 22573F, 1969.

The pore-formers useful for forming microporous wall 12 in the environment of use include solids and pore-forming liquids. In the latter expression, the term for this invention generically embraces semi-solids and viscous fluids. The pore-formers can be inorganic or organic and the wall forming polymer usually contains from 5 to 95% by weight. The term pore-former for both solids and liquids include substances that can be dissolved, extracted or leached from the microporous precursor wall by fluid present in the environment of use to form operable, open-celled type microporous walls. Additionally, the pore-formers suitable for the invention include pore-formers that can be dissolved, leached, or extracted without causing physical or chemical changes in the polymer. The pore-forming solids have a size of about 100 angstroms to 200 microns, and they include alkali metal salts such as lithium carbonate, sodium chloride, sodium bromide, sodium carbonate, potassium chloride, potassium sulfate, potassium phosphate, sodium benzoate, sodium acetate, sodium citrate, potassium nitrite, and the like. The alkaline earth metal salts such as calcium phosphate, calcium nitrate, calcium chloride, and the like. The transition metal salts such as ferric chloride, ferrous sulfate, zinc sulfate, cupric chloride, manganese fluoride, manganese fluorosilicate, and the like. Organic compounds such as polysaccharides including pentoses, hexoses, disaccharides, sugars, sucrose, glucose, fructose, mannitol, mannose, galactose, aldohexose, altrose, talose, sorbitol, and the like, carboxy-polymethylene, Carbowax® compounds, polysorbate, and the like. The pore-formers are non-toxic and on their removal from the wall, channels or paths are formed through wall 12, that fill with fluid. The paths become a means, or diffusional path for diffusion of agent, or drug from the system. The pores extend from inside wall 12 to the outside of wall 12 for effective release of agent or drug to the exterior of system 10.

Additional microporous materials for forming wall 12 include microporous poly(urethanes), cross-linked, chain-extended microporous poly(urethanes), microporous poly(urethanes) in U.S. Pat. No. 3,524,753, microporous poly(imides), microporous poly(benzimidazoles), regenerated microporous proteins, semisolid cross-linked microporous poly(vinylpyrrolidone), microporous materials prepared by diffusion of multivalentcations into polyelectrolyte sols as in U.S. Pat. No. 3,565,259, anisotropic permeable microporous materials of ionically associated polyelectrolytes, microporous polymers formed by the coprecipitation of a polycation and a polyanion as described in U.S. Pat. Nos. 3,276,589; 3,541,006; 3,541,055; and 3,546,142, microporous derivatives of poly(stryrene) such as microporous poly(sodium styrene-sulfonate) and microporous poly(vinyl benzyltrimethyl-ammonium chloride), the microporous materials disclosed in U.S. Pat. Nos. 3,615,024 and U.S. Pat. Nos. 3,646,178 and 3,852,224.

The selective permeable polymers used for partition 14 and wall 12a, when a semipermeable polymer is used for their manufacture in system 10, include, polymers permeable to fluid present in system 10 and the environment, while remaining impermeable to solutes, agents and drugs. Typical materials include semipermeable polymers, also known to the art as osmosis membranes. The semipermeable polymers include cellulose acylate, cellulose diacylate, cellulose triacylate, cellulose ethers and cellulose esters. Typical semipermeable polymers include cellulose acetate, cellulose acetate ethyl carbamate, and the like. Other semipermeable polymers include polyurethane, and selectively permeable polymers formed by the coprecipitation of a polyanion and a polycation, and semipermeable ion exchange polymers. Generally, semipermeable polymers useful for forming partition 14, or wall 12a, will have a fluid permeability of $10^{-5}$ to $10^{-1}$ (cc mil/cm$^2$ hr atm) expressed per atmosphere of hydrostatic or osmotic pressure difference across 14 or 12a at the temperature of use.

Exemplary polymers suitable for partition 14, when it is impermeable to fluid agents and solutes include, plasticized polyvinyl chloride, styrene-butadiene block copolymer, polyesterpolyethers, ethylene-propylene copolymer, segmented block polyurethane, chlorinated polyethylene, ethylene vinylchloride copolymer, and the like. The partition in both designs, can contain a plasticizer to increase its flexibility during use.

Exemplary plasticizers suitable for adding to partition 14 to impart flexibility and stretchability include cyclic and acyclic plasticizers. Typical plasticizers are those selected from the group consisting of phthalates, phosphates, citrates, adipates, tartrates, sebacates, succinates, glycolates, glycerolates, benzoates, myristates, sulfonamides, halogenated phenyls, glycols, diols, and polyols.

Exemplary plasticizers further include dialkyl phthalates, dicycloalkyl phthalates, diaryl phthalates and mixed alkyl-aryl phthalates as represented by dimethyl phthalate, dipropyl phthalate, di(2-ethylhexyl)-phthalate, di-isopropyl phthalate, diamyl phthalate and dicapryl phthalate; alkyl and aryl phosphates such as tributyl phosphate, trioctyl phosphate, tricresyl phosphate, trioctyl phosphate, tricresyl phosphate and triphenyl phosphate; tricresyl phosphate, trioctyl phosphate; tricresyl phosphate, trioctyl phosphate, tricresyl phosphate and triphenyl phosphate; alkyl and aryl phosphates such as tributyl phosphate, trioctyl phosphate, tricresyl phosphate, trioctyl phosphate, tricresyl phosphate and triphenyl phosphate; alkyl citrate and citrates esters such as tributyl citrate, triethyl citrate, and acetyl triethyl citrate; alkyl adipates such as dioctyl adipate, diethyl adipate and di(2-methoxyethyl)-adipate; dialkyl tartrates such as diethyl tartrates and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phythayl ethyl glycolate, butyl phthalyl butyl glycolate, ethylene glycol diacetate, triethylene glycol dibutyrate and triethylene glycol dipropionate. Other plasticizers include camphor, N-ethyl-(o- and p-tolune) sulfonamide, chlorinated biphenyl, benzophenone, N-cyclohexyl-ptoluene sulfonamide, substituted epoxides, poly(alkylene glycols), poly(alkylene diols), esters of alkylene glycols, and the like.

Suitable plasticizers can be selected for blending with partition 14 forming materials by selecting plasticizers that have a high degree of solvent power for the materials, are compatible with the materials over both the processing and use temperature ranges, exhibit permanence as seen by a strong tendency to remain in the plasticized partition and imparts flexibility to the partition. Procedures for selecting a plasticizer having the described characteristics are disclosed in the *Encyclopedia of Polymer Science and Technology*, Vol. 10, pages 228 to 306, 1979, published by John Wiley & Sons, Inc., New York. Also, a detailed description pertaining to the measurement of plasticizer properties, including solvent parameters and compatibility, the Hildebrand solubility parameter, the Flory-Huggins interaction parameter, and the cohesive-energy density, CED, parameter is disclosed in *Plasticization and Plasticizer Processes, Advances in Chemistry Series* 48, Chapter 1, pages 1 to 26, 1965, published by the American Chemical Society, Washington, D.C. The amount of plasticizer added generally is an amount sufficient to produce the desired film and it will vary according to the plasticizer and the materials. Usually about 0.001 parts up to 25 parts, or higher, of the plasticizer can be used for 100 parts partition forming material with a presently preferred range of 0.1 part to 15 parts of plasticizer, or mixtures thereof for 100 parts of partition forming materials.

The swellable polymer that can be used as driving member 18 for expanding and enlarging space 16, and for pushing partition 14, as in FIGS. 2a and 2b, into agent space 15, or for swelling and expanding while correspondingly decreasing the agent containing space, are generally lightly cross-linked hydrophilic polymers. These polymers, or swelling, reduce the amount of space available for agent 17, and this continual decrease in space acts to substantially maintain agent 17 in a substantially saturated phase. The formulation and maintenance at the agent microporous wall boundary layer in system 10, at substantially the same rate and amount throughout the release period, produces for system 10, a prolonged zero order rate.

Representative polymers are those that swell in the presence of fluid to a high degree without dissolution, are lightly cross-linked, usually exhibiting a 5 to 50 fold volume increase. Exemplary polymers are cross-linked hydrogels including poly(hydroxyalkylmethacrylates), poly(acrylamide), poly(methacrylamide), poly(N-vinyl-2-pyrrolidone), anionic and cationic hydrogels, polyelectrolyte complexes, a water-insoluble, water-swellable copolymer produced by forming a dispersion of finely divided copolymers of maleic anhydride with styrene, ethylene, propylene, butylene or isobutylene cross-linked with from about 0.001 to about 0.5 moles of a polyunsaturated cross-linking agent per mole of maleic anhydride in the copolymer as disclosed in U.S. Pat. No. 3,989,586, the water-swellable polymers of N-vinyl lactams as disclosed in U.S. Pat. No. 3,992,562, semi-solid cross-linked poly(vinyl pyrrolidone), diester cross-linked polyglucan hydrogels as described in U.S. Pat. No. 4,002,173, the anionic hydrogels of heterocyclic N-vinyl monomers as disclosed in U.S. Pat. No. 4,036,788, the ionogenic hydrophillic gels as described in *J. Biomedical Mater. Res.*, Vol. 7, pages 123 to 126, 1973, and the like.

The osmotically effective compound that can be used in space 16, when partition 14 is formed of a polymer selected from the group consisting of a semipermeable and impermeable polymer, and when wall 12a is made of a semipermeable polymer include organic and inorganic compounds or solutes that exhibit an osmotic pressure gradient across semipermeable wall 12a against fluid in the environment, or across a semipermeable partition 14 against fluid in agent space 15. Osmotically effective compounds useful for this purpose include magnesium sulfate, magnesium chloride, sodium chloride, lithium chloride, potassium sulfate, sodium carbonate, potassium acid phosphate, mannitol, urea, sucrose, and the like. The osmotically effective compounds are also known as osmagents and they are disclosed in U.S. Pat. Nos. 3,854,770 and 4,077,407. These patents are assigned to the Alza Corporation of Palo Alto, Calif.

The expressions "active agent" and "beneficial agent" as used herein broadly include any compound, composition of matter, or mixture thereof, that can be delivered from system 10 to produce a beneficial and useful result. The active agents include air purifiers, algicides, antioxidants, biocides, catalysts, chemical reactants, cosmetics, contraceptives, drugs, disinfectants, food supplements, fermentation agents, fertility inhibitors, fertility promoters, fungicides, germicides, herbicides, insecticides, micro-organism attenuators, pheremones, pro-drugs, plant growth inhibitors, pesticides, preservatives, rodenticides, sex sterilants, slimicides, vitamins and other agents that benefit the environment of use and mankind.

Representative of drugs that can be delivered by system 10 include tranquilizers such as reserpine, thropropazate, perphenazine and chloropromazine; psychic energizers such as amitriplyline, imipramine and methylphenidate; analgesicsantipyretics such as aspirin, phenacetin and salicylamide indomethacin, and diclofenac; anti-inflammatories such as hydrocortisone, dexamethazone, prednisolone, and phenylbutazone; decongestants such as phenylephrine and pseudoephedrine; antibiotics such as erythromycin, tetracycline, minocyline, etc., cardiovascular drugs such as quinidine; and other agents.

Representatve of drugs that can be dispensed in the vagina from a system sized, shaped and adapted for easy insertion and comfortable retention in the vagina include allantorn, aminocacridine hydrochloride, benzocaine, benzalkonium chloride, candicidin, dienestrol., dibucaine, ephedrine sulfate, furazolidone, gentain violet, hydrocortisone, methylbenzethium chloride, phenylmercuric acetate, providone-iodine, sulfanilamide, sulfisoxazole, tetracaine, undecylenate, and the like. See *Techniques of Medication*, by Eric W. Martin, pages 106 to 107, 1969, published by J. B. Lippincott Company, Philadelphia.

Representative of drugs that can be dispensed in the ano-rectal environment from a system shaped, sized and adapted for easy insertion and comfortable retention therein include acetarsol, adrenaline with benzocaine, aminophylline, aminophylline with phenobarbitol sodium, ampicillin, aspirin, astroscopolamine, belladonna, benzocaine, bisacodyl, bismuth subgallate, caffeine, ergotamine tartrate, chloralhydrate, chlorpromazine, cinchocaine, cyclomethycaine sulfate, dimenhydrinate, hydrocortisone, ichthammol, isoprenaline, metronidazole, morphine, oxymorphine hydrodiamine, thiethylperzaine meleate, and the like. See *Martindale The Extra Pharmacopolia*, Edited by Ainley Wade, General Index, page 2056, 1977, published by the Pharmaceutical Press, London; and, *National Drug Code Directory*, 1972, published by Public Health Service, U.S. Department of Health, Education and Welfare, Washington, D.C.

The drug present in system 10 can be in various forms, such as uncharged molecules, molecular complexes, pro-drug, pharmacological acceptable salts such as hydrochlorides, hydrobromides, sulfate, laurylate, palmitate, phosphate, nitrate, borate, acetate, maleate, tartrate, oleates, and salicylate. For acidic drugs, salts of metals, amines, or organic cations, for example, quaternary ammonium salts can be used. Derivatives of drugs such as esters, ethers and amides, which have solubility characteristics suitable for use herein can be used. The agent or drug can be in the compartment as a suspension, dispersion, paste, cream, particle, granule, emulsion, solution, powder, and the like.

The amount of agent in system 10 is preferably initially in excess of the amount that can be dissolved in fluid that enters the agent housing space. Under this physical state, when agent 17 is in excess, system 10 will diffusingly operate to give a substantially constant rate of release over time, then member 18 activates and the combined action of member 18 and system 10 operating as a unit system producing a substantially constant rate of release over a prolonged period of time. The length of time agent is released can also be varied by having different amounts of agent in system 10 to form saturated solutions containing saturated concentrations of agent for delivery from the system 10. Generally, system 10 can house from 0.01 ng to 7 g or more, with individual devices containing for example 25 ng, 1 mg 100 mg, 250 mg, 500 mg, 1.5 g., 5 g, 7.5 g, 7.5 g, 10 g, and the like.

The systems of the invention are manufactured by standard techniques. For example, in one embodiment a swellable polymer or a compressed amount of an osmotic solute are independently coated on one surface with a partition forming polymer, and then a compressed amount of agent, having a shape that corresponds to the shape of the polymer or solute. Next, a microporus wall forming the system can be applied by molding, spraying or dipping the system intermediate into a wall forming material to completely surround the intemediate and yield the system. In another embodiment, a microporous wall can be partly cast in a preshaped mold to the desired dimension defining the wall that surrounds an internal space, the space partly filled with a mass of agent, followed by a layer of a partition and then a mass of a driving force. The remainder of the wall abutting the driving force, is formed from a microporus or semipermeable polymer for closing the device. Walls forming the system also can be joined by various joining techniques, such as high frequency electronic sealing that provides clean edges and firmly formed walls. Another, and presently preferred technique that can be used is the air suspension procedure. Air suspension preocedures are described in U.S. Pat. No. 2,799,241; in *J. AM. PHARM. ASSOC.*, Vol 49, pages 82 to 84, 1960. Other wall forming techniques include pan coating, in which the materials are deposited by successive tumbling and spraying of the polymer solution on the agent and the driving member tumbling in a rotating pan. Other standard manufacturing procedures are described in *Modern Plastic Enclyclopedia,* Vol. 46, pages 62 to 70, 1069; and in *Pharmaceutical Sciences,* by Remington, 14th Ed., pages 1626 to 1678 1970, published by Mack Publishing Company, Easton, Penna.

Exemplary solvents suitable for manufacturing the wall, or the partition include inert inorganic and organic solvents that do not adversely harm the wall forming materials, the partition forming materials, and the final device. The solvents broadly include members selected from the group consisting of aqueous solvents, and organic solvents, such as alcohols, ketones, esters, ethers, aliphatic hydrocarbons, halogenated solvents, cycloapliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl ether, ethylene glycol monoethyl acetate, methylene dichloride, ehtylene dichloride, propylene dichloride, carbon tetrachloride, nitroethane, itropropane, tetrachloroethane, ethyl ether, isopropyl either, cyclohexane clyclo-octane, benzene, toluene, naphtha, 1, 4-dioxane, tetrahydrofuran, diglyme, water, and mixtures thereof such as acetone and water, acetone and methanol, acetone and ethyl alcohol, methylene dichloride and methanol, and ethylene dichloride and emethanol.

The following examples are merely illustrative of the present invention that produces devices that keep their physical and chemical integrity during their delivery history, and they should not be considered as limiting the scope of the invention in any way, as this example and other equivalents thereof will become more apparent to those versed in the art in the light of the present disclosure, the drawings, and the accompanying claims.

EXAMPLE 1

First, 125 mg of the osmotic solute sodium chloride is compressed to a preselected shape and coated on one of its surface with a partition forming composition comprising 70% cellulose acetate having an acetyl content of 32% mixed with 30% polyethylene glycol having a molecular weight of 400 dissolved in methylene chloride methanol, 80:20, wt:wt, until an expandable partition is formed on the solute.

Next, 235 mg of dry antiarrhythmic and antifirbrillatory p-amino-N(2-diethylamineothyl)-benzamide hydrochloride having a molecular weight of 271.19 is compressed into a shape that corresponds to the shape of the solute, and placed onto the available surface of the partition. Next the device intermediate comprising of the solute, partition and drug is surrounded with a microporous wall. The microporous wall is formed form a composition consisting of 65 g of cellulose acetate having an acetyl content of 32%, 41 g of the poreformer sorlitol, 11.7 g of polyethylene glycol 400, and a wall forming solvent consisting 1900 ml of acetone and 375 ml of water. The wall is formed by air tumbling until a 7 mil thick microporous wall is formed on the system to produce a system manufactured as an oral device.

EXAMPLE 2

A therapeutic system is manufactured in the form of an oral device for delivering procainamide hydrochloride to the gastrointestinal tract or a warm-blooded animal as follows: first, 200 mg of lightly cross-linked, water swellable, water insoluble polyvinyl alcohol is coated on one surface with a layer of partition forming composition consisting of 70% cellulose acetate having an acetyl content of 32% mixed with 30% polyethylene glycol having a molecular weight of 400 and dissolved in methylene chloride: methanol, 80:20, wt:wt, until a semipermeable partition is formed. Next, 235 mg of procainamide hydrochloride having a molecular weight of 271.79 is pressed onto the partition in the form of a solid mass having a shape corresponding to the shape of the polyvinyl alcohol. Then the just-formed drug-polymer composite device intermediate is surrounded on all surfaces, except the surface of the polymer distant from the partition, with a wall of microporous polymeric polypropylene having a void volume of 0.565 to 0.075 $cm^3/gm$, a density of 0.60 to 0.85 $gm/cm^3$, and a pore size of 150 to 5000 angstroms, as disclosed in U.S. Pat. No. 3,426,754. Finally, the exposed surface of the polyvinyl alcohol polymer is coated with a wall of cellulose acetate having an acetyl content of 38.3% to yield the device.

EXAMPLE 3

The device of example 1 is manufactured in this example, except that in this example, the partition is formed of highly plasticized poly(monochloroethylene).

EXAMPLE 4

The procedures of example 1 and 2 are repeated with all conditions as previously described, except the agent in the agent space is selected from the group consisting of hypnotics, sedatives, psychic energizers, tranquilizers, anticonvulsants, muscle relaxants, antiparkinson, analgesics, anti-inflammatory, anesthetic, muscle contractants, anti-microbiols, antimalarials, hormones, sympathomimetic, duiretics, hypoglcmics and nutritional agents.

EXAMPLE 5

A device for orally adminstering a useful drug is made as follows: first, 500 mg of dry, quinidine is pressed in a Manesty tableting machine to a Stroke's hardness of about 8 kg. Then, 350 mg of lightly cross-linked poly(hydroxyalkyl methacrylate), having a shape corresponding to the shape of the drug, is pressed firmly onto one surface of the drug, to yield the device intermediate. Next, a microporous wall of poly(vinyl chloride) with continuous diffusional paths is prepared by leaching a sheet of polymer consisting on the poly(vinyl chloride) containing the pore forming agent poly (p-dimethylamino styrene). The wall is formed by casting in a solvent of cyclohexane and the solvent evaporated. Then, an aqueous acidic solution of hydrochloric acid is used to leach the pore formers and yield the microporous wall. The leaching is carried out at room temperature followed by washing with distilled water to remove the acid. The device intermediate is surrounded with the wall to yield the device.

The novel systems of this invention uses an expandable member for the obtainment of precise diffusional release rates and enhanced delivery of agent to environments of use while simultaneously maintaining the integrity and character of the systems. And, while there has been described and pointed out features of the invention as applied to presently preferred embodiments, those skilled in the art will appreciate that various modifications, changes, additions and omissions in the device illustrated and described that can be made without departing from the spirit of the invention.

The claims:

1. A system for the controlled delivery of a beneficial agent to an environment of use, the system comprising:
   a. a wall having a plurality of micropaths through the wall, the wall surrounding and forming:
   b. an internal compartment;
   c. a flexible partition in the compartment joined to the wall, said partition forming a first internal space and a second internal space within the compartment;
   d. a beneficial agent in the first space; and,
   e. means in the second space for increasing the volume of said second space, which means are a member selected from the group consisting essentially of an osmotically effective solute and a swellable lightly cross-linked polymer.

2. The system for the controlled delivery of the beneficial agent according to claim 1, wherein the micropaths in the wall are formed when the system is in the environment of use, which micropaths are connected to a multiplicity of micropores in the wall.

3. The system for the controlled delivery of the beneficial agent according to claim 1, wherein when the device is in the environment of use, the micropaths fill with fluid present in the environment, and the agent in the system diffuses through the fluid filled paths to the exterior of the system.

4. The system for the controlled delivery of the beneficial agent according to claim 1, wherein in operation when the system is in a fluid environment, agent is delivered from the system by diffusion through fluid filled micropaths in the wall, with the member absorbing fluid into the second space, expanding, continuously filling the space and moving against the partition, urging it to expand into the first space for substantially maintaining the concentration of agent in a saturated phase at the microporous wall, thereby, delivering agent at a zero order rate over an increased length of time.

5. The system for the controlled delivery of the beneficial agent according to claim 1, wherein the partition is formed of a semipermeable polymer selected from the group consisting of a cellulose ester, cellulose ether, cellulose acylate, cellulose diacylate, and cellulose triacylate.

6. The system for the controlled delivery of the beneficial agent according to claim 1, wherein the partition is formed of a polymer impermeable to the passage of agent, solute, polymer and fluid.

7. The system for the controlled delivery of the agent according to claim 1, wherein the agent is a drug selected from the group consisting of local acting drugs and systemic acting drugs.

8. The system for the controlled delivery of the agent according to claim 1, wherein the agent is a drug, the environment is the gastrointestional tract, and the system is manufactured as a device sized, shaped and adapted for orally administering the drug to the gastrointestional tract.

9. The system for the controlled delivery of the agent according to claim 1, wherein the agent is a drug, the environment is a body passageway, and the system is sized, shaped and structured for easy placement and prolonged retention in the body passageway.

10. The system for the controlled delivery of the beneficial agent according to claim 1, wherein the partition contains a plasticizer.

11. The system for the controlled delivery of the beneficial agent according to claim 1, wherein the swellable polymer is lightly cross-linked and is a member selected from the group consisting of poly(hydroxyalkyl methacrylate), poly(acrylamide), poly(N-vinylpyrrolidone), anionic hydrogels, cationic hydrogels, and water-insoluble hydrophilic polymers.

12. The system for the controlled delivery of the beneficial agent at a controlled rate according to claim 1, wherein the wall is formed of a microporous polymer selected from the group consisting of poly(urethane), poly(imides), poly(sulfone), and poly(saccharides).

13. The system for the controlled delivery of the beneficial agent according to claim 1, wherein the micropaths in the wall are formed by removing a pore-former having size of about 100 angstroms to 200 microns.

14. A process for manufacturing a device for dispensing a useful agent, which device delays the appearance of a receding diffusional boundary layer when the device is dispensing the agent in an environment of use, the process comprising the steps of:
a. shaping and compressing and amount of the useful agent into a preselected shape:
b. shaping a swellable and expandable polymer into dimensions corresponding to the shaped agent;
c. placing a partition formed of a flexible polymer between the shaped agent and the shaped swellable polymer;
d. positioning the shaped agent and the shaped polymer in contacting relation with the partition; and,
e. surrounding the shaped agent and the shaped polymer with a microporous wall to yield the device.

15. A process for delaying the appearance of a receding diffusional boundary layer in a device that dispenses a beneficial agent to an environment of use, wherein the device comprises:
a. microporous wall surrounding and forming:
b. a compartment;
c. a flexible partition in the compartment joined to the wall, said partition dividing the compartment into a first space and a second space;
d. a beneficial agent in the first space;
e. a volume generating agent in the second space, said volume generating agent a member selected from an osmotically effective solute and a expandable, swellable lightly cross-linked polymer: and wherein the process for delaying the apearance of the receding boundary comprises;
  1. expanding the volume generating agent in the second space to increase the volume of the second space causing it to move the partition into the first space and correspondingly diminish the volume occupied by the first space; thereby,
  2. maintaining the beneficial agent in a saturated state at the microporous wall for an increased length of time, which state delays the appearance of the receding diffusional boundary layer.

16. A diffusor for the controlled and continuous delivery of a beneficial agent at a zero order rate of release for an increased length of time to a fluid environment of use, the diffusor comprising;
a. a wall having a multiplicity of micropaths therethrough, the wall surrounding and forming;
b. a compartment having an internal space;
c. a beneficial agent in the compartment occupying part of the space;
d. a expandable polymer in the compartment occupying the remainder of the space;
e. a flexible partition in the compartment united to the wall and placed between the beneficial agent and the expandable polymer; and,
f. wherein, when the diffussor is in the fluid environment, fluid fills the micropaths and enters space occupied by the expandable polymer, which absorbs the fluid causing it to expand against the partition, causing the partition to push the beneficial agent towards the wall, for keeping it in a saturated state, thereby increasing the length of time the beneficial agent is released from the diffusion at a zero order rate of release.

17. The diffusor for the controlled and continuous delivery of agent according to claim 16, wherein the environment of use is a human, the fluid is a biological fluid, the agent is a drug, and the diffusor is sized, shape and structured for placement and retention in said environment.

18. The diffusor for the controlled and continuous delivery of agent according to claim 16, wherein the micropaths in the wall are formed in the environment of use by fluid leaching a pore-former from the wall.

19. The diffusor for the controlled and continuous delivery of a beneficial agent according to claim 16, wherein the agent is a member selected from the group consisting of tranquilizers, psycic energizers, analgesics, antipyretics, anti-inflammatories, hormones, oral drugs, vaginal drugs and ano-rectal drugs.

* * * * *